(12) United States Patent
Rodríguez Pierluissi et al.

(10) Patent No.: US 10,173,974 B1
(45) Date of Patent: Jan. 8, 2019

(54) NATURAL PRODUCT-BASED SYNTHESIS OF NOVEL ANTI-INFECTIVE ISOTHIOCYANATE- AND ISOSELENOCYANATE-FUNCTIONALIZED AMPHILECTANE DITERPENES

(71) Applicants: Abimael D. Rodríguez Pierluissi, San Juan, PR (US); Karinel Nieves Merced, San Juan, PR (US)

(72) Inventors: Abimael D. Rodríguez Pierluissi, San Juan, PR (US); Karinel Nieves Merced, San Juan, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 15/345,402

(22) Filed: Nov. 7, 2016

Related U.S. Application Data

(60) Provisional application No. 62/251,275, filed on Nov. 5, 2015.

(51) Int. Cl.
| | |
|---|---|
| *A61P 31/10* | (2006.01) |
| *A61P 33/00* | (2006.01) |
| *C07C 331/02* | (2006.01) |
| *C07C 391/00* | (2006.01) |

(52) U.S. Cl.
CPC ............ *C07C 331/02* (2013.01); *A61P 31/10* (2018.01); *A61P 33/00* (2018.01); *C07C 391/00* (2013.01); *C07C 2603/28* (2017.05)

(58) Field of Classification Search
CPC combination set(s) only.
See application file for complete search history.

(56) References Cited

PUBLICATIONS

Ciavatta et al. "Structural and stereochemical revision of isocyanide and isothiocyanate amphilectenes from the Caribbean marine sponge *Cribochalina* sp." Tetrahedron 2005, 61, 8049-8053. (Year: 2005).*
Aviles et al. "Synthesis and preliminary biological evaluation of a small library of hybrid compounds based on Ugi isocyanide multicomponent reactions with a marine natural product scaffold" Biorg. Med. Chem. Lett. 2015, 25, 5339-5343 (Year: 2015).*

* cited by examiner

*Primary Examiner* — Amanda L Aguirre
(74) *Attorney, Agent, or Firm* — Hoglund & Pamias, PSC; Roberto J. Rios

(57) ABSTRACT

The marine natural product (−)-8,15-diisocyano-11(20)-amphilectene, isolated from the Caribbean sponge *Svenzea flava*, was used as scaffold to synthesize five new products, all of which were tested against laboratory strains of *Plasmodium falciparum* and *Mycobacterium tuberculosis* $H_{37}Rv$. The scaffold contains two isocyanide units that are amenable to chemical manipulation, enabling them to be elaborated into a small library of sulfur and selenium compounds. The scaffold along with its isothio- and isoselenocyanate analogs has low to sub-micro molar antiplasmodial activity.

14 Claims, 10 Drawing Sheets

NATURAL PRODUCT-BASED SYNTHESIS OF NOVEL ANTI-INFECTIVE ISOTHIOCYANATE- AND ISOSELENOCYANATE-FUNCTIONALIZED AMPHILECTANE DITERPENES

GOVERNMENT INTEREST

The claimed invention was made with U.S. Government support under grant number 1SC1GM086271-01A1 awarded by the National Institutes of Health (NIH). The government has certain rights in this invention.

BACKGROUND OF THE INVENTION

Tuberculosis and Malaria are two of the world's deadliest diseases, with more than two million deaths worldwide in 2013, most of them in sub-Saharan Africa, South-East Asia and Western Pacific regions. Plasmodium falciparum has for some time been developing resistance against known antimalarial drugs, and therefore new drugs are urgently needed. Chloroquine was the first drug produced on a large scale for treatment and prevention of malaria infection. Chloroquine has activity against the blood stages of Plasmodium ovale, P. malariae, and susceptible strains of P. vivax and P. falciparum. Widespread resistance in most malaria-endemic countries has led to a continual decline in its use for the treatment of P. falciparum, although it remains effective for treatment of P. ovale, P. malariae, and, in most regions, P. vivax.

Tuberculosis (TB) is second only to HIV/AIDS as the greatest killer worldwide due to a single infectious agent, Mycobacterium tuberculosis (Mtb). Standard antimycobacterial drugs (isoniazid, rifampicin, pyrazidamide, ethambutol, streptomycin) have been used for decades, and resistance to the medicines is also widespread. If a patient is unable to tolerate isoniazid, or if isoniazid-resistant TB is present, rifampicin, ethambutol, and pyrazidamide are usually used for 18 months. If rifampicin-resistant TB is present, the regimen usually consists of isonizaid, ethambutol, and pyrazidamide for 18 months. If there is resistance to both isoniazid and rifampicin, the disease is very difficult to treat. Disease strains that are resistant to a single anti-TB drug have been documented in every country surveyed. In some cases more severe drug resistance can develop. Extensively drug-resistant TB, XDR-TB, is a form of multi-drug resistant tuberculosis (MDR-TB) that responds to even fewer available medicines, including the most effective second-line anti-TB drugs. About 480,000 people developed MDR-TB in the world in 2013. More than half of these cases were in India, China and the Russian Federation. It is estimated that about 9.6% of MDR-TB cases had XDR-TB. Hence, the search for new antitubercular drugs is a priority so as to overcome the problem of drug resistance and to finally eradicate TB.

The marine sponge metabolite (−)-8,15-diisocyano-11 (20)-amphilectene 1 (see FIG. 1) was first reported by Faulkner et al. from Hymeniacidon amphilecta in 1978, and has been shown subsequently to exhibit potent in vitro anti-infective activity. Several structurally related natural products as well as a small number of synthetic analogs prepared from diisocyanide 1 also exhibit antimalarial and antimycobacterial potential. While comparison among their activities reveals that the biological activity is generally dependent on the presence of the isocyanide functionality, the structural features of the carbon backbone and the location of the isocyanide groups also seem to play a pivotal role. Notwithstanding, the observation that a plethora of sponge-derived isocyanide-, isothiocyanate-, isocyanate-, and formamide-containing diterpenoids based on amphilectane, cycloamphilectane, isocycloamphilectane, and isoneoamphilectane skeletons are often active (usually in the low nanomolar range), suggests that the biological activity does not depend strictly on the presence of the isocyanide functionality. This observation implies that the metabolite's carbon skeleton can also modulate biological activity.

As part of the inventor's drug discovery program in search of new agents for the treatment of Malaria and Tuberculosis, we became interested in the synthesis of a limited number of amphilectane-based isothiocyanate and isoselenocyanate diterpenes for biological evaluation. Of the two classes of congeneric compounds, organic isoselenocyanates are of particular interest since so far they have received much less attention compared to their sulfur and oxygen analogs. diisocyanide 1 was targeted as a suitable starting material, a well-known antimalarial and antimycobacterial pharmacophore which contains both a rigid amphilectane skeleton and two isocyanide "handles" with potential for further synthetic elaboration. It was anticipated that comparison among the biological activities exhibited by the strickly related amphilectane analogs with those of 1 would reveal definite structure-activity relationships. While the isothiocyanate moiety is found in many natural products only two isothiocyanate-containing amphilectane diterpenoids with antiplasmodial activity have been documented. Remarkably, no studies assessing the potential antiplasmodial or antimycobacterial properties of isoselenocyanate-containing compounds (synthetic or natural) have been reported so far.

SUMMARY OF THE INVENTION

According to the present invention, the syntheses of analogs 2-6 were swiftly accomplished through the isothio- and isoselenocyanation of metabolite 1, previously isolated from the marine sponge Svenzea flava. All compounds were characterized by detailed inspection of $^1$H NMR, $^{13}$C NMR, DEPT-NMR, 2D NMR (COSY, HSQC, HMBC, and NOESY), mass spectrometry, and UV and IR spectra.

The purity of these compounds was ascertained by TLC, HPLC and spectroscopic analysis. All of the semi-synthetic derivatives exhibited strong to potent in vitro inhibition of Plasmodium falciparum Dd2 and 3D7 strains with some exhibiting greater antiplasmodial activity than the standard drug chloroquine. Likewise, the new compounds have shown sub-micromolar to low micromolar in vitro antimycobacterial activity. In order to assess their microbe-specific selectivity (i.e. whether the observed antimicrobial activity was a specific or general toxic effect) the cytotoxic effects of compounds 1-6 using a mammalian Vero cell line were also investigated. The results obtained are further evidence of the anti-infective activity of these novel amphilectane-based chemotypes.

BRIEF DESCRIPTION OF THE DRAWINGS

Further features and advantages of the invention will become apparent from the following detailed description taken in conjunction with the accompanying figures showing illustrative embodiments of the invention, in which.

Figure 1:
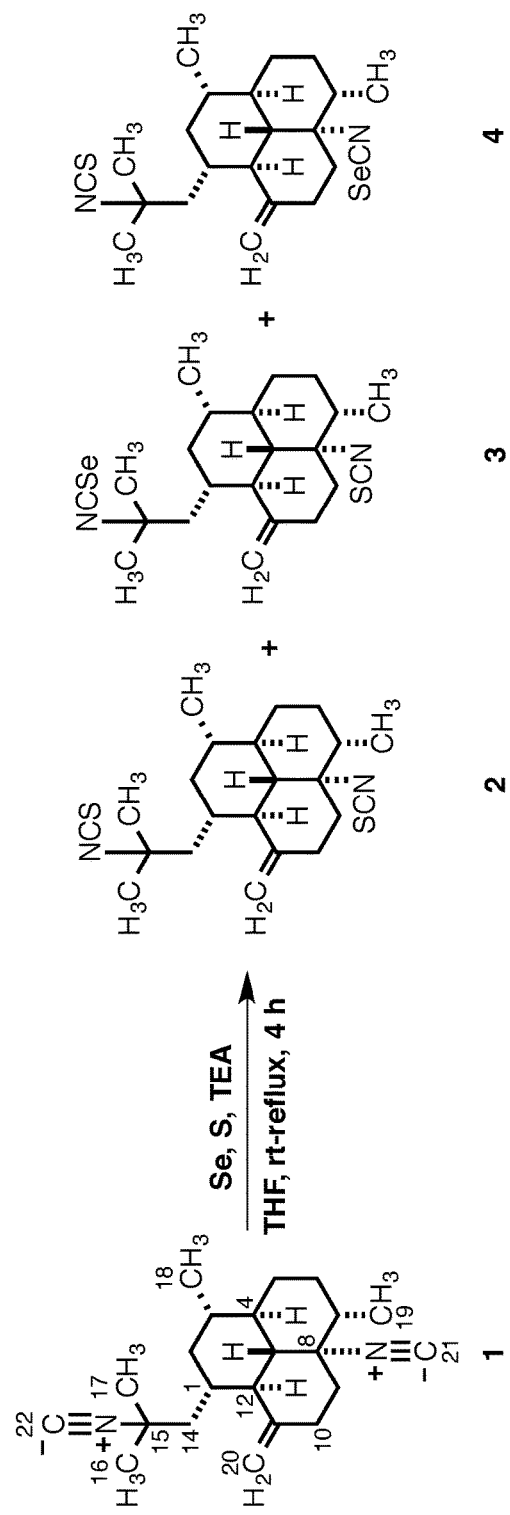
FIG. 1 shows the synthesis of Isothiocyanate Analogs 2-4, according to the present invention.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

Experimental Data
General Techniques

All of the reactions requiring anhydrous conditions were conducted in flame-dried glass apparatus under an atmosphere of argon. Column chromatography (CC) was performed on silica gel (35-75 µm); reactions were followed by TLC analysis using glass pre-coated silica gel plates with fluorescent indicator (254 nm) and visualized with a UV lamp or $I_2$ vapors. Semipreparative RP-HPLC was performed using a UV detector set at 254 nm and a column with 5 µm, 250×4.6 mm size with a flow rate of 1.0 mL/min. THF and commercially available reagents were purchased and used as received without further purification. Optical rotations were recorded with a polarimeter using a 0.5 mL capacity cell with 1 dm path length. Infrared spectra were recorded using thin films supported on NaCl discs. $^1$H and $^{13}$C NMR spectra were recorded in Fourier transform mode at the specified field strength on a 700 MHz spectrometer. Spectra were obtained on CDCl$_3$ solutions in 5 mm diameter tubes, and chemical shifts are quoted in parts per million relative to the residual signals of chloroform ($\delta_H$=7.26 ppm, $\delta_C$=77.0 ppm). Multiplicities in the $^1$H NMR spectra are described as follows: s=singlet, d=doublet, t=triplet, q=quartet, m=multiplet, br=broad; coupling constants are reported in hertz. High-resolution mass spectrometry (HRMS) was performed using a quadrupole mass analyzer, and the data are reported with ion mass/charge (m/z) ratios as values in atomic mass units. Yields shown are based on recovered starting material.

Animal Material

The Caribbean sponge *Svenzea flava* (phylum Porifera; class Demospongiae; order Halichondrida; family Dictyonellidae) was collected at a depth of 89 feet by scuba off Mona Island, Puerto Rico, in July 2006. A voucher specimen (no. IM06-04) is stored at the Chemistry Department of the University of Puerto Rico, Rió Piedras Campus. The species *Svenzea flava* was originally classified as *Pseudoaxinella flava*. Despite lacking dark granulous cells that are a signature characteristic of other species within the genus *Svenzea*, it has been accepted as *Svenzea flava*.

Isolation and Purification of
(−)-8,15-Diisocyano-11(20)-amphilectene (1)

The known sponge metabolite (−)-8,15-diisocyano-11 (20)-amphilectene (1) was obtained pure as white crystals (528 mg) from freshly collected sponge specimens as previously described (the sponge was originally reported by our group as *Hymeniacidon* sp.). The structure characterization of 1 was established on the basis of IR, UV, [α]$_D$, MS, and $^1$H and $^{13}$C NMR spectroscopic analyses.

Synthesis of Isothiocyanate-Containing Amphilectanes

To a 25° C. solution of diisocyanide 1 (37.0 mg, 0.11 mmol) in dry THF (5.0 mL) was added selenium (0.9 mg, 0.01 mmol), sulfur (4.0 mg, 0.12 mmol), and TEA (76 µL, 0.5 mmol). After refluxing for 4 h the reaction mixture was allowed to cool to 25° C. and then concentrated in vacuo. The crude oil obtained was purified by flash-silica gel CC with 100% hexane to afford unreacted 1 (23 mg) followed by another fraction consisting of a mixture of isothiocyanate-containing products that was purified by HPLC (MeOH/ H$_2$O, 88/12). Retention times were 20.4 min for the more polar mixture of 3 and 4 (10 mg, 53%) and 23.8 min for the less polar compound 2 (3.0 mg, 18%).

8,15-Diisothiocyano-11(20)-amphilectene (2)

Colorless oil; [α]$^{20}_D$ −108.0 (c 0.25, CHCl$_3$); UV (MeOH) $\lambda_{max}$ (ε) 202 (19471) nm; IR (film) $\nu_{max}$ 2926, 2857, 2095, 1728, 1459, 1262 cm$^{-1}$; $^1$H NMR (700 MHz, CDCl$_3$) δ 4.87 (br s, 1H, H-20β) 4.61 (br s, 1H, H-20α), 2.34 (m, 1H, H-9β) 2.26 (m, 2H, H-10), 2.16 (m, 1H, H-2β) 2.06 (dd, J=1.3, 14.6 Hz, 1H, H-14β), 2.00 (m, 1H, H-5β), 1.89 (m, 1H, H-1), 1.75 (t, J=10.8 Hz, 1H, H-12), 1.55 (m, 2H, H-6), 1.47 (s, 3H, H-17), 1.44 (s, 3H, H-16), 1.43-1.35 (br envelope, 2H, H-7, H-9α), 1.28 (m, 1H, H-14α), 1.11-1.00 (br envelope, 3H, H-3, H-4, H-13), 0.99 (d, J=6.3 Hz, 3H, H-19), 0.94 (d, J=6.1 Hz, 3H, H-18), 0.92-0.83 (br envelope, 2H, H-2α, H-5α); $^{13}$C NMR (175 MHz, CDCl$_3$) δ 150.2 (C, C-11), 131.1 (C, C-21), 130.4 (C, C-22), 106.1 (CH$_2$, C-20), 69.6 (C, C-8), 60.6 (C, C-15), 56.9 (CH, C-13), 46.8 (CH$_2$, C-14), 46.7 (CH, C-12), 43.3 (CH, C-4), 42.5 (CH, C-7), 41.1 (CH$_2$, C-2), 40.1 (CH$_2$, C-9), 35.7 (CH, C-3), 34.1 (CH$_2$, C-10), 33.2 (CH, C-1), 31.9 (CH$_3$, C-17), 30.5 (CH$_2$, C-6), 29.9 (CH$_2$, C-5), 29.4 (CH$_3$, C-16), 19.9 (CH$_3$, C-18), 16.1 (CH$_3$, C-19); EI-LRMS m/z [M]$^+$ 388 (3), 330 (27), 329 (22), 271 (100), 255 (26), 215 (58), 201(30), 159 (31); EI-HRMS m/z calcd for C$_{22}$H$_{32}$N$_2$S$_2$ [M]$^+$ 388.2007, found 388.2007.

8-Isothiocyano-15-isoselenocyano-11(20)-amphilectene (3) and 8-Isoselenocyano-15-isothiocyano-11(20)-amphilectene (4) (2:3 Mixture of Isomers)

White solid; UV (MeOH) $\lambda_{max}$ (ε) 192 (962), 202 (4457) nm; IR (film) $\nu_{max}$ 2920, 2870, 2255, 2096, 1453 cm$^{-1}$; $^1$H NMR (700 MHz, CDCl$_3$) (major isomer) δ 4.88 (br s, 1H, H-20β) 4.63 (br s, 1H, H-20α), 2.40-1.99 (br envelope, 6H, H-2β, H-5β, H-9β, H-10αβ, H-14β), 1.90 (m, 1H, H-1), 1.75 (m, 1H, H-12), 1.60-1.26 (br envelope, 5H, H-6αβ, H-7, H-9α, H-14α), 1.47 (s, 3H, H-17), 1.44 (s, 3H, H-16), 1.14-0.84 (br envelope, 5H, H-2α, H-3, H-4, H-5α, H-13), 1.00 (d, J=6.4 Hz, 3H, H-19), 0.95 (d, J=6.2 Hz, 3H, H-18); (minor isomer) δ 4.87 (br s, 1H, H-20β) 4.59 (br s, 1H, H-20α), 2.40-1.99 (br envelope, 6H, H-2β, H-5β, H-9β, H-10αβ, H-14β), 1.90 (m, 1H, H-1), 1.75 (m, 1H, H-12), 1.60-1.26 (br envelope, 5H, H-6αβ, H-7, H-9α, H-14α), 1.51 (s, 3H, H-17), 1.44 (s, 3H, H-16), 1.14-0.84 (br envelope, 5H, H-2α, H-3, H-4, H-5α, H-13), 0.99 (d, J=6.3 Hz, 3H, H-19), 0.96 (d, J=6.1 Hz, 3H, H-18); $^{13}$C NMR (175 MHz, CDCl$_3$) (major isomer) δ149.8 (C, C-11), 130.4 (C, C-22), 124.4 (C, C-21), 106.4 (CH$_2$, C-20), 71.0 (C, C-8), 60.6 (C, C-15), 56.7 (CH, C-13), 46.8 (CH$_2$, C-14), 46.6 (CH, C-12), 43.3 (CH, C-4), 42.3 (CH, C-7), 41.1 (CH$_2$, C-2), 39.8 (CH$_2$, C-9), 35.7 (CH, C-3), 33.9 (CH$_2$, C-10), 33.2 (CH, C-1), 31.9 (CH$_3$, C-17), 30.4 (CH$_2$, C-6), 29.8 (CH$_2$, C-5), 29.5 (CH$_3$, C-16), 19.8 (CH$_3$, C-18), 16.1 (CH$_3$, C-19); (minor isomer) δ 150.1 (C, C-11), 131.2 (C-21), 122.4 (C, C-22), 106.1 (CH$_2$, C-20), 69.6 (C, C-8), 61.3 (C, C-15), 56.9 (CH, C-13), 46.7 (CH, C-12), 46.5 (CH$_2$, C-14), 43.2 (CH, C-4), 42.5 (CH, C-7), 41.0 (CH$_2$, C-2), 40.1 (CH$_2$, C-9), 35.6 (CH, C-3), 34.0 (CH$_2$, C-10), 33.1 (CH, C-1), 31.6 (CH$_3$, C-17), 30.5 (CH$_2$, C-6), 29.9 (CH$_2$, C-5), 29.0 (CH$_3$, C-16), 19.9 (CH$_3$, C-18), 16.0 (CH$_3$, C-19); EI-LRMS m/z [M]$^+$ 436 (31), 330 (34), 329 (46), 271 (95), 270 (85), 255 (100), 215 (88), 201 (65), 159 (42); EI-HRMS m/z calcd for C$_{22}$H$_{32}$N$_2$S$^{80}$Se [M]$^+$ 436.1451, found 436.1459. Multiple attempts to separate the mixture of regioisomers 3 and 4 by normal- and reversed-phase HPLC proved unsuccessful.

General Procedure for Synthesis of Isoselenocyanate-Containing Amphilectanes.

General Procedure A

To a 25° C. solution of diisocyanide 1 (12.0 mg, 0.04 mmol) in dry THF (2.0 mL) was added selenium (6.0 mg, 0.08 mmol) and TEA (0.07 mL, 0.5 mmol). After stirring for 24 h the reaction mixture was concentrated in vacuo and the crude oil obtained was purified by flash-silica gel CC using a 99:1 mixture of hexane/EtOAc to afford 5 as the sole product (14 mg, 78%).

General Procedure B

To a 25° C. solution of diisocyanide 1 (16.0 mg, 0.05 mmol) in dry THF (2.0 mL) was added selenium (8.0 mg, 0.1 mmol) and TEA (0.1 mL, 0.7 mmol). After refluxing for 12 h the reaction mixture was allowed to cool to 25° C. and then concentrated in vacuo. The crude oil obtained was purified by flash-silica gel CC using a 99:1 mixture of hexane/EtOAc to afford a fraction consisting of a mixture of two products that was subsequently purified by HPLC (MeOH/H$_2$O, 95/5). Retention times were 8.32 min for compound 5 (12.0 mg, 50%) and 9.29 min for compound 6 (6.0 mg, 33%).

8,15-Diisoselenocyano-11(20)-amphilectene (5)

Colorless oil; [α]$^{20}$D −139.0 (c 1.0, CHCl$_3$); UV (MeOH) λ$_{max}$ (ε) 202 (56143) nm; IR (film) ν$_{max}$ 2921, 2870, 2258, 2110, 1455 cm$^{-1}$; $^1$H NMR (700 MHz, CDCl$_3$) δ 4.89 (br s, 1H, H-20β) 4.60 (br s, 1H, H-20α), 2.38 (m, 1H, H-9β) 2.30 (m, 1H, H-10β), 2.24 (m, 1H, H-10α), 2.17 (m, 1H, H-2β) 2.10 (dd, J=1.2, 14.7 Hz, 1H, H-14β) 2.02 (m, 1H, H-5β), 1.91 (m, 1H, H-1), 1.75 (t, J=10.9 Hz, 1H, H-12), 1.52 (s, 3H, H-17), 1.49 (s, 3H, H-16), 1.48-1.32 (br envelope, 5H, H-6αβ, H-7, H-9α, H-14α), 1.14-1.02 (br envelope, 3H, H-3, H-4, H-13), 1.01 (d, J=6.3 Hz, 3H, H-19), 0.96 (d, J=6.3 Hz, 3H, H-18), 0.93-0.83 (br envelope, 2H, H-2α, H-5α); $^{13}$C NMR (175 MHz, CDCl$_3$) δ 149.7 (C, C-11), 124.5 (C, C-21), 122.5 (C, C-22), 106.4 (CH$_2$, C-20), 70.9 (C, C-8), 61.3 (C, C-15), 56.6 (CH, C-13), 46.7 (CH, C-12), 46.6 (CH$_2$, C-14), 43.3 (CH, C-4), 42.3 (CH, C-7), 41.0 (CH$_2$, C-2), 39.8 (CH$_2$, C-9), 35.6 (CH, C-3), 33.9 (CH$_2$, C-10), 33.2 (CH, C-1), 31.6 (CH$_3$, C-17), 30.4 (CH$_2$, C-6), 29.8 (CH$_2$, C-5), 29.1 (CH$_3$, C-16), 19.8 (CH$_3$, C-18), 16.1 (CH$_3$, C-19); EI-LRMS m/z [M]$^+$ 484 (28), 378 (23), 377 (21), 272 (45), 271 (100), 270 (86), 255 (97), 215 (94), 201 (82), 199 (65), 159 (68); EI-HRMS m/z calcd for C$_{22}$H$_{32}$N$_2$$^{80}$Se$_2$ [M]$^+$ 484.0896, found 484.0902.

8-Isoselenocyanoamphilecta-11(20),15-diene (6)

Colorless oil; [α]$^{20}$D+70.0 (c 0.2, CHCl$_3$); UV (MeOH) λ$_{max}$ (ε) 202 (9039) nm; IR (film) ν$_{max}$ 2922, 2852, 2264, 2093, 1452 cm$^{-1}$; $^1$H NMR (700 MHz, CDCl$_3$) δ 4.86 (s, 1H, H-20β) 4.76 (s, 1H, H-16β), 4.67 (s, 1H, H-16α), 4.66 (s, 1H, H-20α), 2.59 (d, J=14.3 Hz, 1H, H-14β), 2.38 (m, 1H, H-9β) 2.29 (m, 2H, H-10), 2.01 (m, 1H, H-5β), 1.80 (m, 1H, H-2β) 1.76 (m, 2H, H-1, H-12), 1.72 (s, 3H, H-17), 1.54 (m, 3H, H-6αβ, H-14α), 1.41 (m, 2H, H-7, H-9α), 1.04 (m, 3H, H-3, H-4, H-13), 1.00 (d, J=6.4 Hz, 3H, H-19), 0.90 (d, J=5.9 Hz, 3H, H-18), 0.86 (m, 1H, 5α), 0.70 (m, 1H, 2α); $^{13}$C NMR (175 MHz, CDCl$_3$) δ 149.7 (C, C-11), 144.2 (C, C-15), 123.8 (C, C-21), 111.3 (CH$_2$, C-16), 106.1 (CH$_2$, C-20), 70.9 (C, C-8), 56.7 (CH, C-13), 46.5 (CH, C-12), 43.6 (CH, C-4), 43.0 (CH$_2$, C-14), 42.3 (CH, C-7), 39.8 (CH$_2$, C-2), 39.6 (CH$_2$, C-9), 36.0 (CH, C-3), 33.9 (CH, C-1), 33.8 (CH$_2$, C-10), 30.5 (CH$_2$, C-6), 29.8 (CH$_2$, C-5), 22.6 (CH$_3$, C-17), 19.7 (CH$_3$, C-18), 16.1 (CH$_3$, C-19); EI-LRMS m/z [M]$^+$ 377 (17), 297 (7), 282 (18), 272 (42), 271 (100), 270 (83), 255 (94), 215 (81), 199 (60), 159 (55), 145 (48), 105 (52), 91 (59); EI-HRMS m/z calcd for C$_{21}$H$_{31}$N$^{80}$Se [M]$^+$ 377.1622, found 377.1626.

Treatment of Diisoselenocyanate 5 with Elemental Sulfur to 8,15-Diisothiocyano-11(20)-amphilectene (2)

To a 25° C. solution of diisoselenocyanate 5 (7.0 mg, 0.01 mmol) in dry THF (2.0 mL) was added sulfur (0.9 mg, 0.03 mmol) and TEA (9.7 μL, 0.07 mmol). After refluxing for 4 h the reaction mixture was allowed to cool to 25° C. and then concentrated in vacuo. The crude oil obtained was purified by flash-silica gel CC with a 98:2 mixture of hexane/EtOAc to afford 2 (4.0 mg, 71%) as the sole product.

Evaluation of Inhibition of *Plasmodium falciparum* Growth

The 3D7 and Dd2 strains of *P. falciparum* malaria (BEI Resources, MR4/ATCC, Manassas, Va.) were cultured in human type O+ erythrocytes in complete medium consisting of RPMI 1640 (Cellgro), 0.043 mg/mL gentamicin (Gibco), 0.014 mg/mL hypoxanthine (Acros), 38.5 mM HEPES (Sigma), 0.18% sodium bicarbonate (Cellgro), 0.20% glucose (MP Biomedical), 0.003 mM NaOH (Sigma), 0.2% Albumax (Gibco), and 5% human serum as previously described. Briefly, cultures were maintained in 25-cm$^2$ flasks (Corning) at a volume of 10 mL, gassed for 30 s with 3% CO$_2$, 1% O$_2$, and 96% N$_2$, and were finally incubated at 37° C. The antimalarial activity was determined with a SYBR Green based parasite proliferation assay as previously described. After 72 h of incubation in the presence of serial dilutions of compounds, the increase of parasite DNA contained in human red blood cells was measured. The relative fluorescence values were measured using a Molecular Devices SpectraMAX Gemini EM fluorimeter (excitation 495 nm, and emission 525 nm). Data were analyzed using Microsoft Excel and were plotted using SigmaPlot 10 (Systat).

Evaluation of Antitubercular Activity

Antimycobacterial activity was determined against Mtb H$_{37}$Rv (ATCC 27 294) in the microplate Alamar blue assay (MABA) system as described previously. The tuberculosis drug rifampicin (RMP) was used as a positive control in the assay.

Cytotoxicity Assay

The cytotoxic activity of tested compounds was determined with the Vero cell line ATCC CRL-1586 using an MTS assay as outlined previously.

Discussion:

As shown in FIG. 1, since aliphatic isocyanides hardly react with elemental sulfur, the desired diisothiocyanate 2 was synthesized via the isothiocyanation of 1 as outlined in Scheme 1. Thus, treatment of diisocyanide 1 with S, $Et_3N$, and catalytic amounts of Se in refluxing THF following a synthetic protocol previously described by Fujiwara and co-workers, afforded 8,15-diisothiocyano-11(20)-amphilectene (2) in 18% yield. Surprisingly, the desired product was accompanied by large amounts of unreacted 1 along with smaller quantities of congeners 3 and 4 (53%), formed as a 2:3 mixture of regioisomers that was inseparable by chromatography (the integration of selected signals in the $^1H$ NMR spectra of the reaction products provided the isomer ratio). Addition of 2.5 mol % of S or increasing the refluxing time up to 16 h failed to afford full conversion to 2 or to preclude the formation of 3 and 4. These results suggest that in this case the reaction might exhibit a low catalytic activity of Se (i.e. the rate determining step appears to be the reaction between 1 and elemental Se and not the Se—S exchange) and that perhaps the amount of Se catalyst to isocyanide should be increased to >10 mol % (vide infra). Even though the reaction was very sluggish, we were delighted to have these compounds at hand since their biological evaluation was at this point of outmost interest to us. As the only differences between 3 an 4 were a result of the —NCS and —NCSe functionalities switching positions, these isomers have nearly identical $^{13}C$ NMR shifts, apart from those at C-8 and C-15 (and their substituents). Nevertheless, we were able to distinguish the terpene isothiocyanate groups from its isoselenocyanate counterparts in 3 (minor) and 4 (major) by the $^{13}C$ chemical shift of the —NCS (129-132 ppm) vs —NCSe (121-125) group. Although these signals are typically of low intensity in the $^{13}C$ NMR spectra (during 1D spectroscopic acquisition an extended delay time (>5 s) and a 90° pulse angle are usually required to enhance their intensity) their detection was easily accomplished with a 700 MHz spectrometer. These noticeable differences in $^{13}C$ NMR spectroscopic data, in combination with 2D NMR experiments (HSQC and HMBC spectra), allowed us to assign the structure of each isomer unambiguously.

Figure 2:
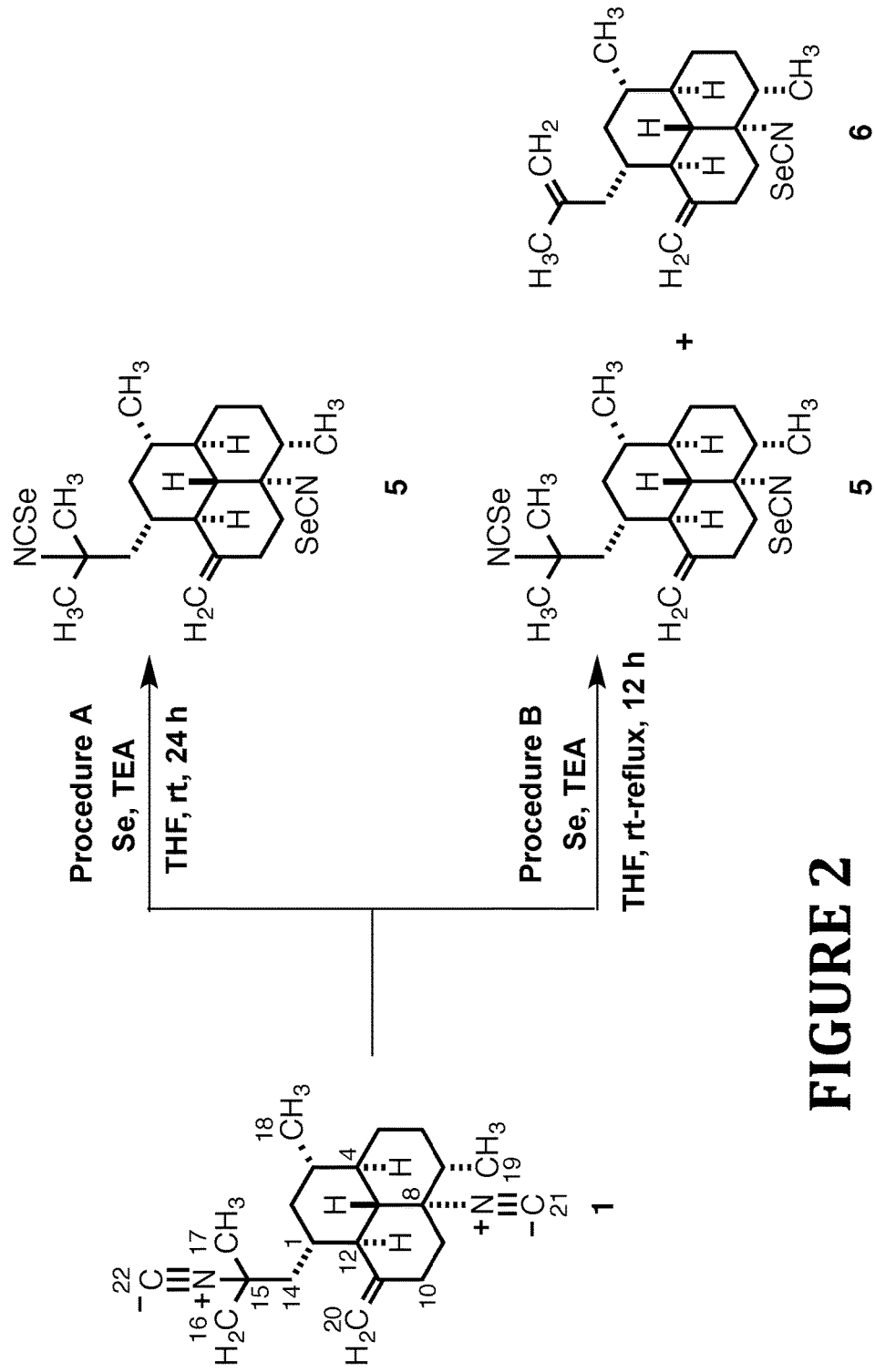
FIG. 2 shows the synthesis of Isoselenocyanate Analogs 5 and 6, according to the present invention.
Figure 3:
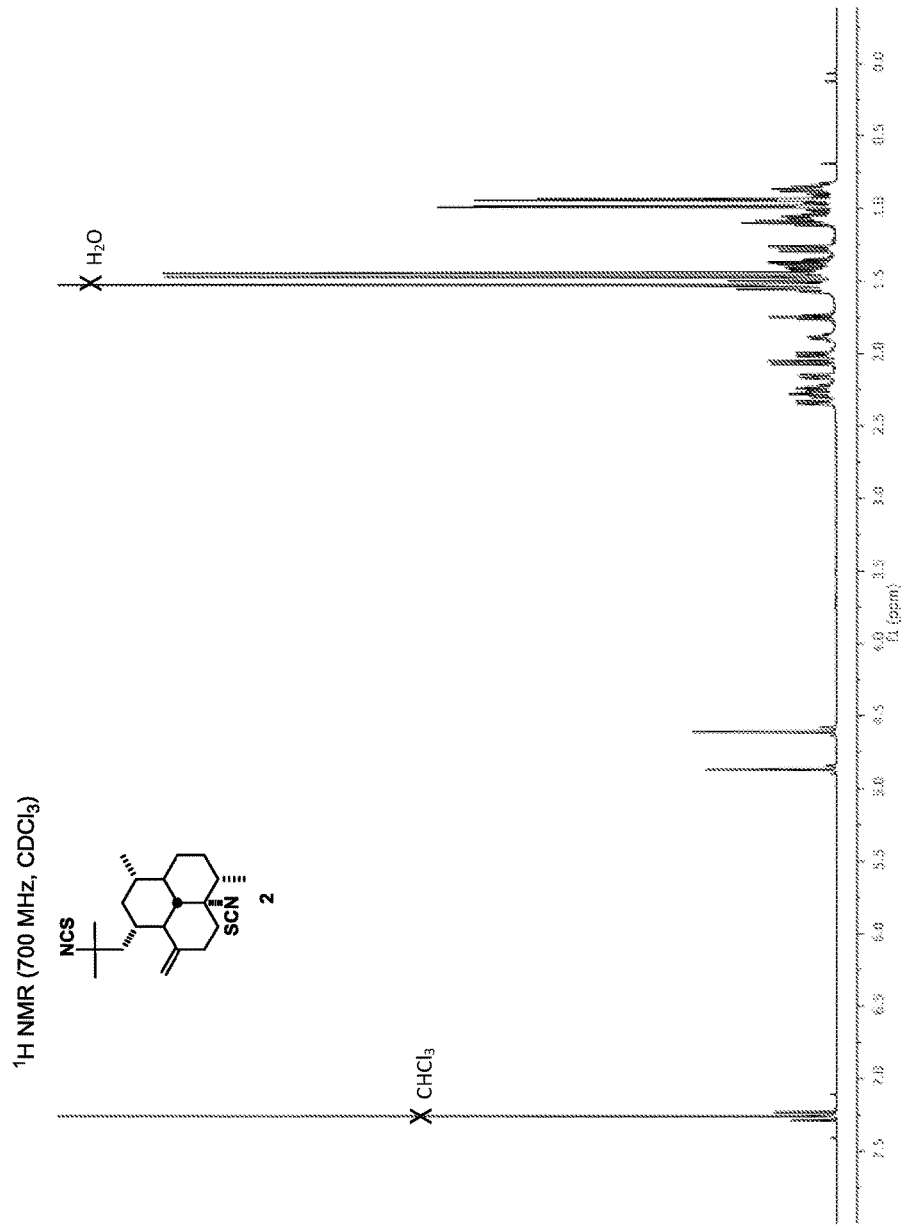
FIG. 3 shows $^1$H NMR spectra of compound 2, according to the present invention.
Figure 4:
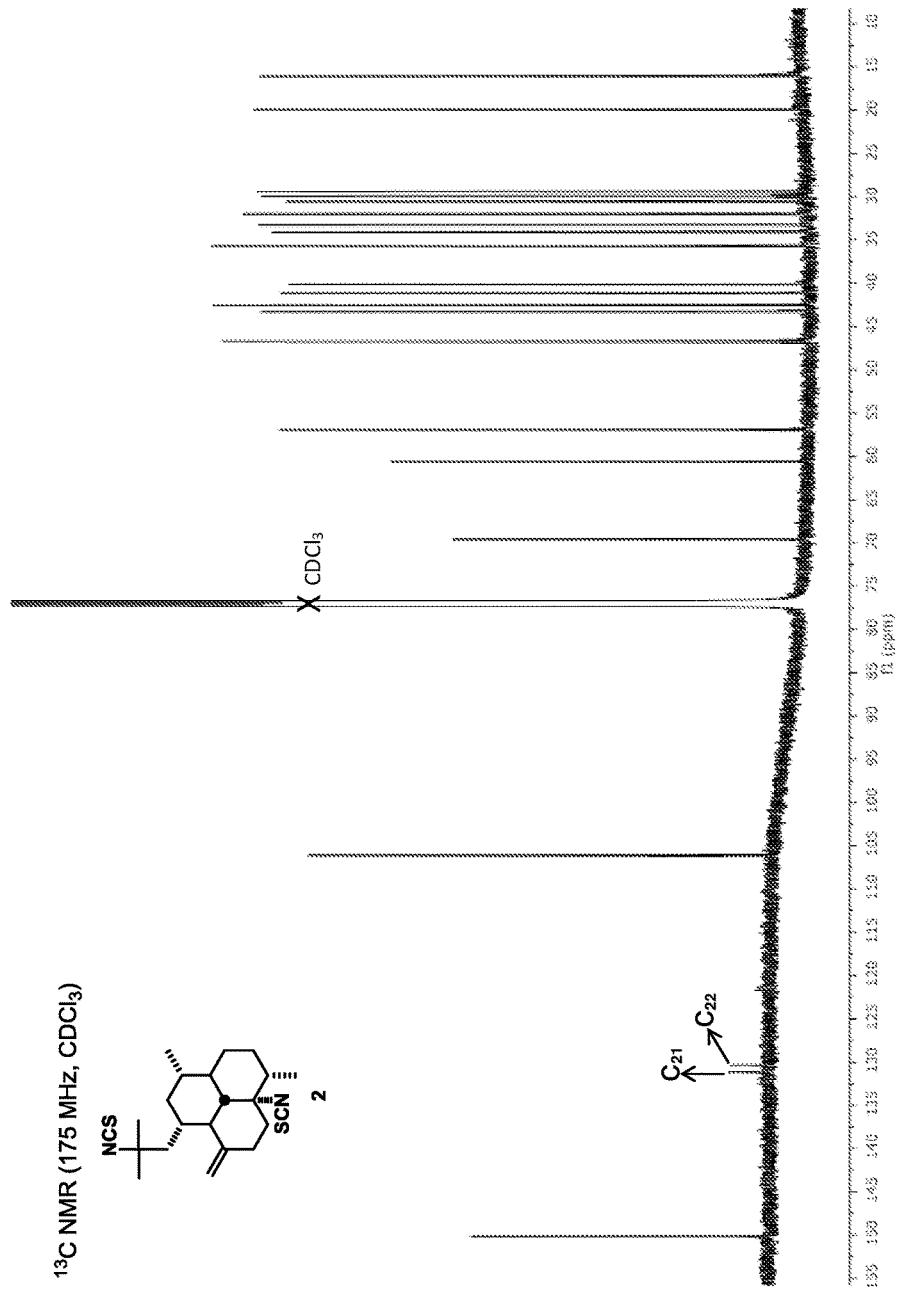
FIG. 4 shows $^{13}$C NMR spectra of compound 2, according to the present invention.
Figure 5:
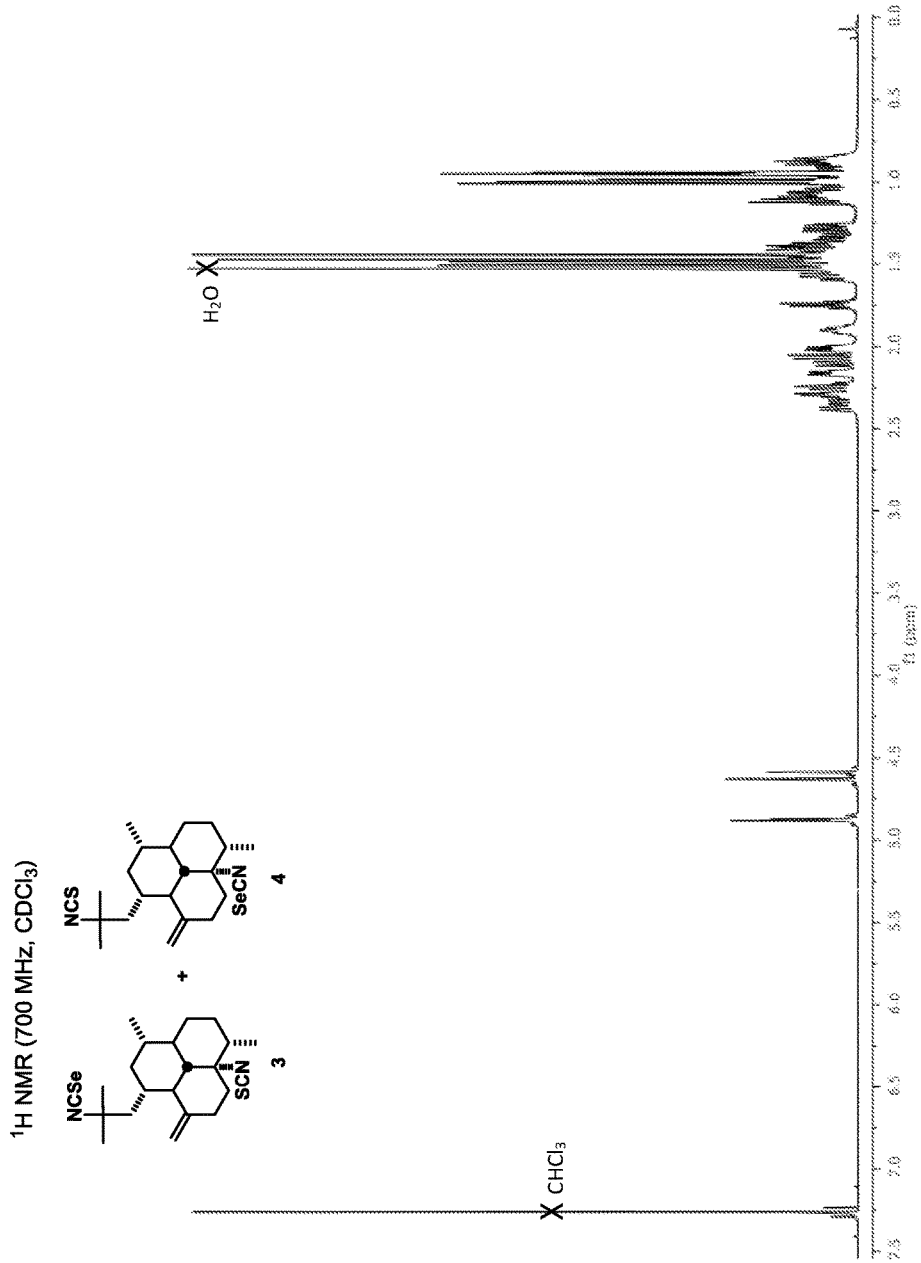
FIG. 5 shows $^1$H NMR spectra of compounds 3 and 4, according to the present invention.
Figure 6:
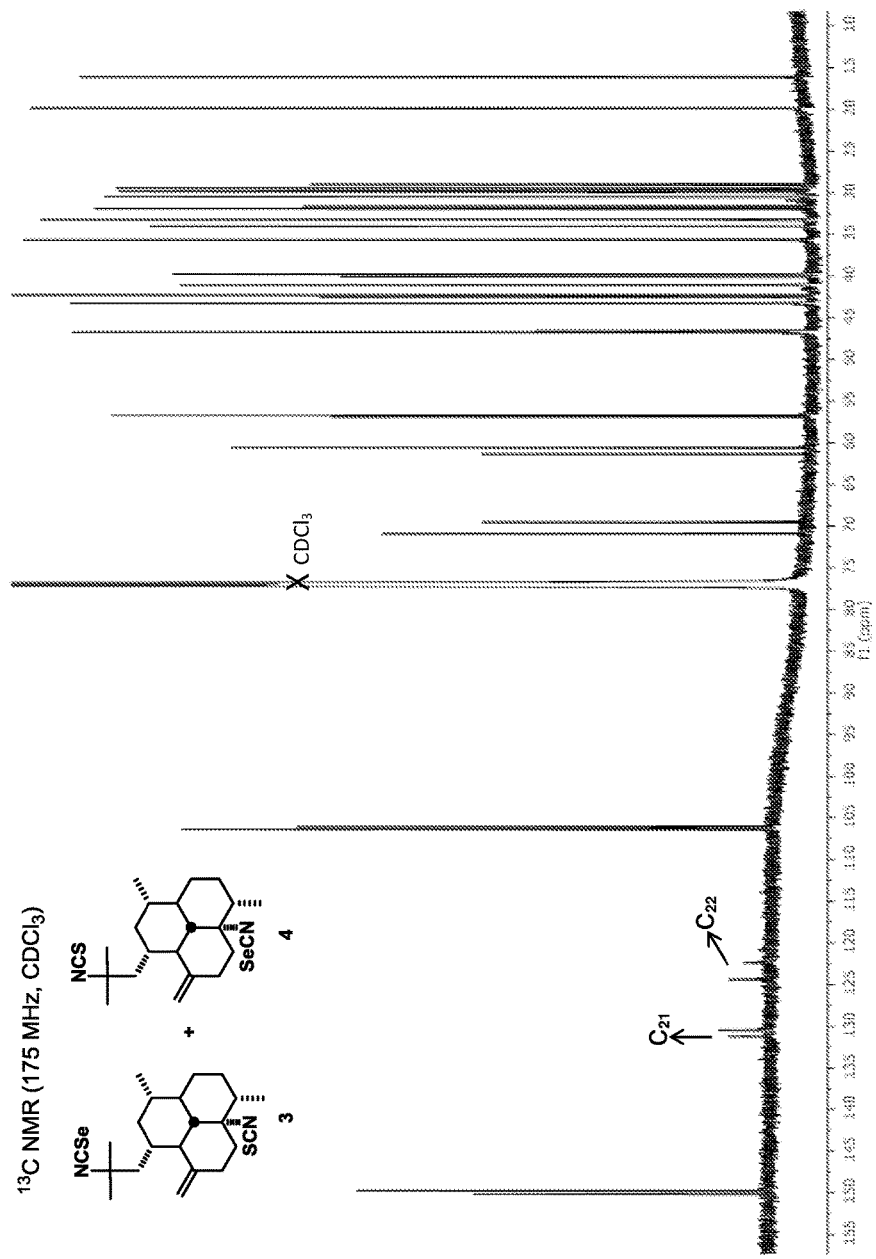
FIG. 6 shows $^{13}$C NMR spectra of compounds 3 and 4, according to the present invention.
Figure 7:
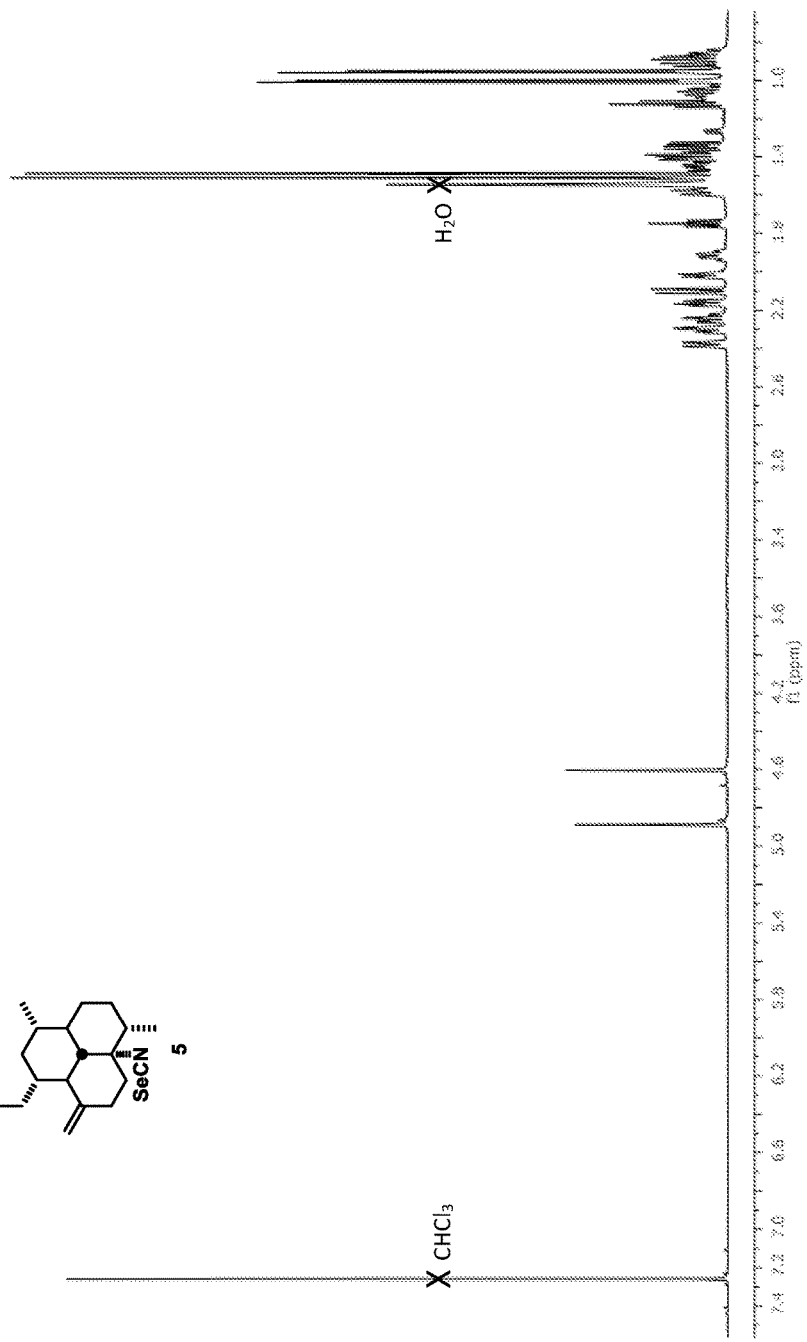
FIG. 7 shows $^1$H NMR spectra of compound 5, according to the present invention.
Figure 8:
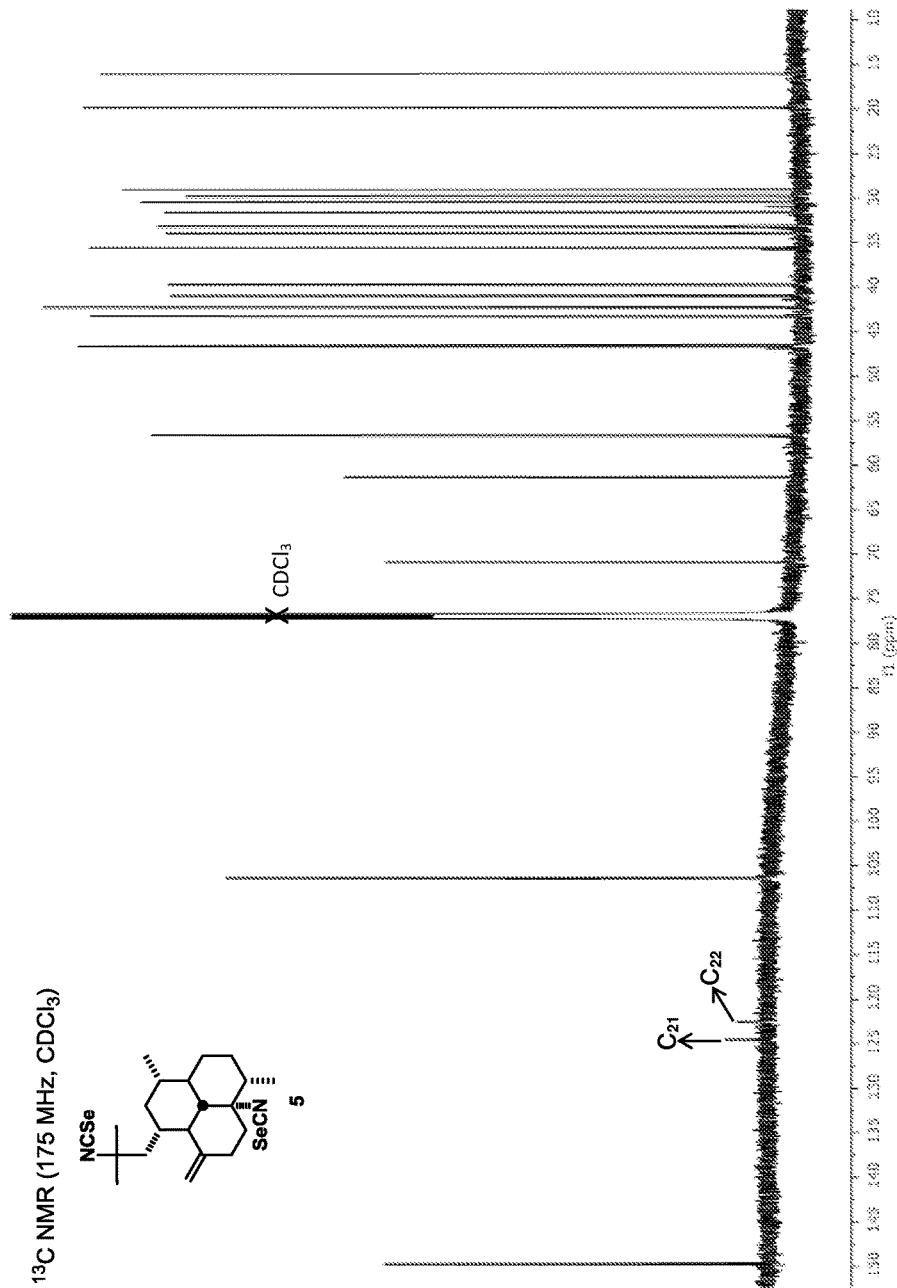
FIG. 8 shows $^{13}$C NMR spectra of compound 5, according to the present invention.
Figure 9:
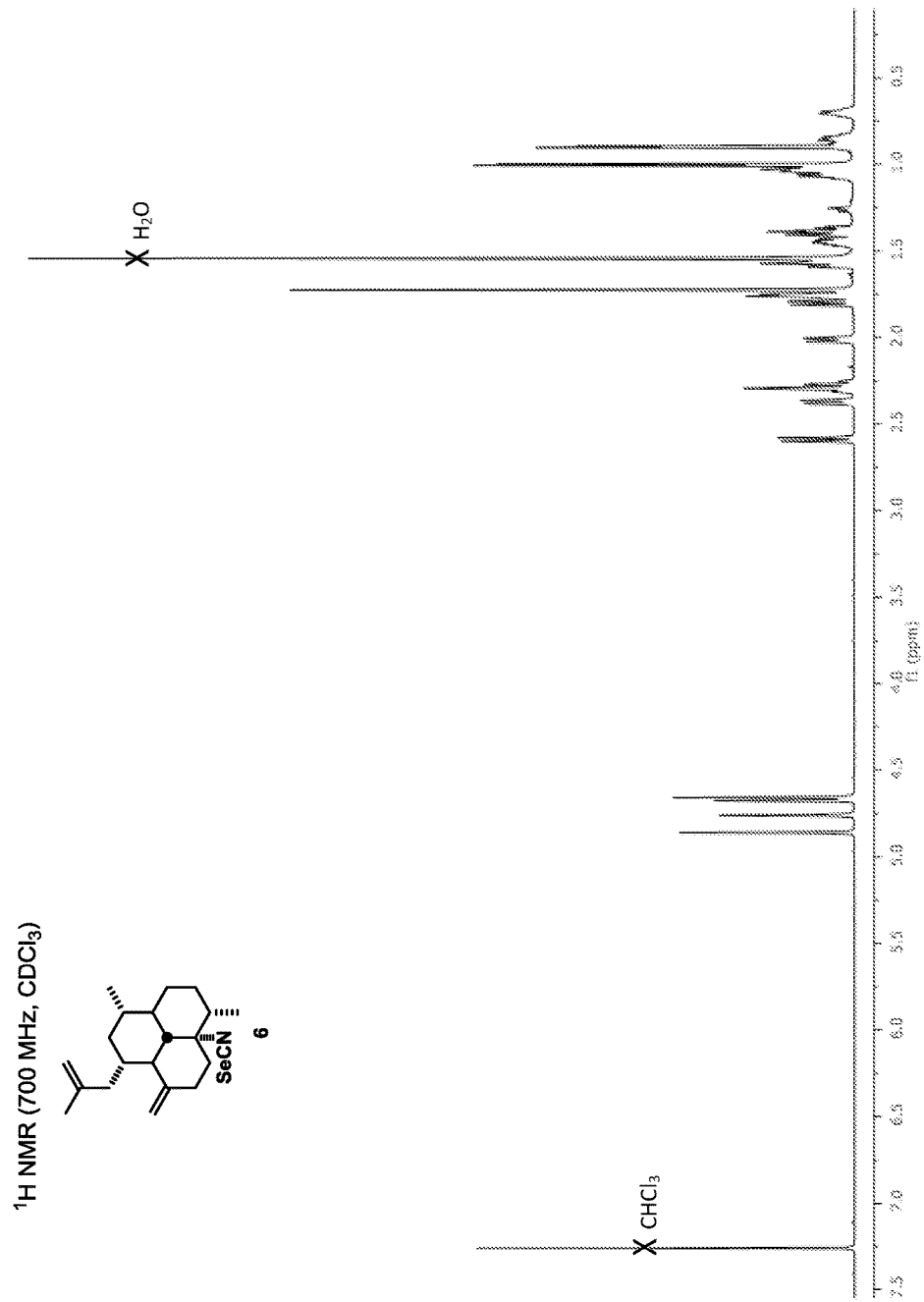
FIG. 9 shows $^1$H NMR spectra of compound 6, according to the present invention.
Figure 10:
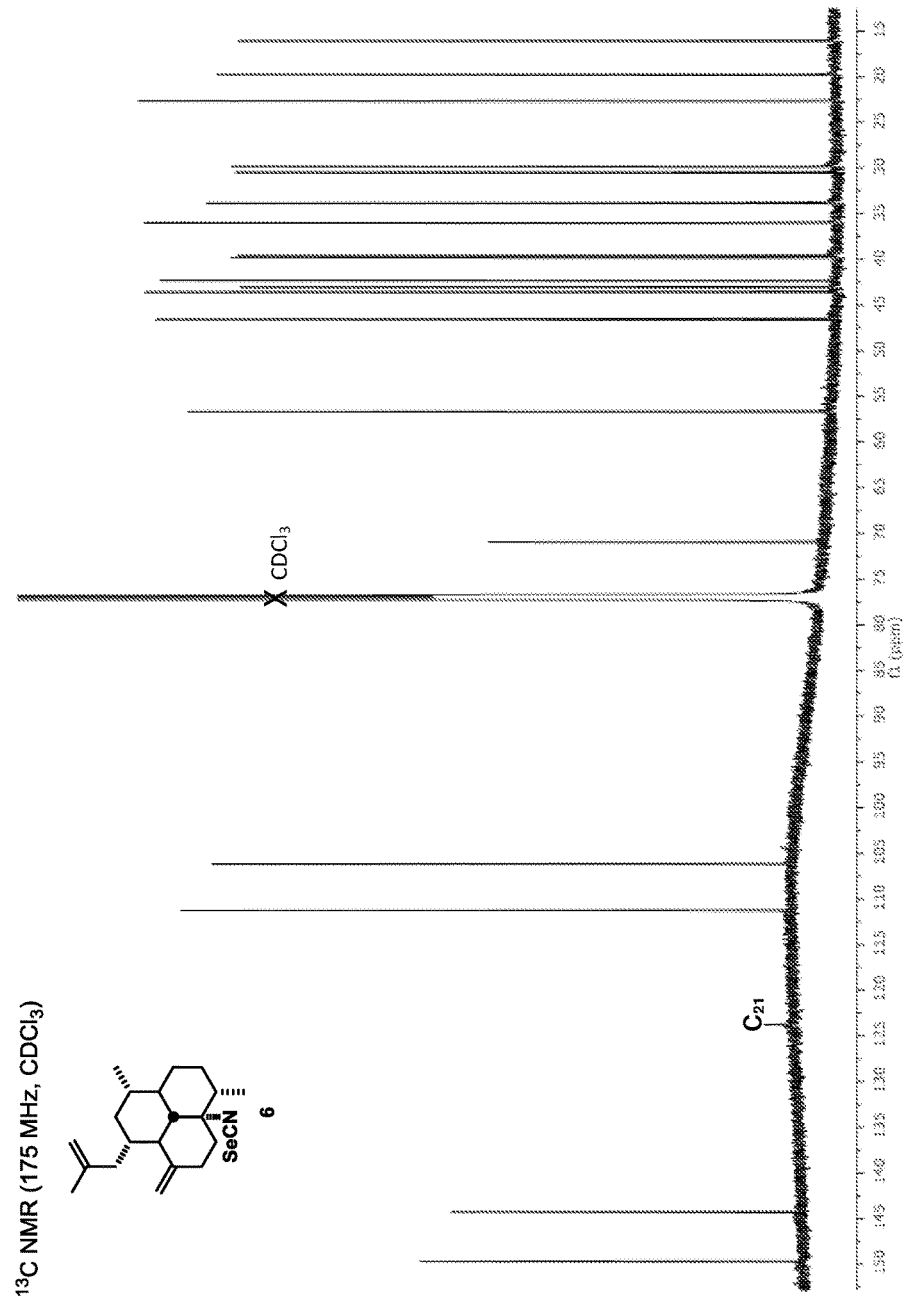
FIG. 10 shows $^{13}$C NMR spectra of compound 6, according to the present invention.

Concomitant with these efforts, we sought to achieve the isoselenocyanation of diisocyanide 1 with elemental selenium in the presence of TEA to give 8,15-diisoselenocyano-11(20)-amphilectene (5) in satisfactory yield. The synthesis and biological evaluation of 5 was very appealing to us since natural products bearing the isoselenocyanate moiety have never been isolated. Furthermore, synthetic isoselenocyanate-containing compounds apparently have never been investigated for potential antiplasmodial or antimycobacterial activity. Thus, insertion of two selenium atom equivalents at C-21 and C-22 of diisocyanide 1 via an isoselenocyanation reaction with Se using TEA in THF at 25° C. led cleanly to 5 (78% yield). Gratifyingly, when the reaction was conducted in refluxing THF diisoselenocyanate 5 (obtained in 50% yield) was accompanied by lesser quantities of isoselenocyanate 6 as a single regioisomer following purification by flash- and HPLC chromatography. In this fashion, the reaction proceeded with selective base-mediated decomposition of 5 at the more reactive C-15 isoselenocyanate group to give 6, albeit in modest yield (33% yield). We welcome the formation of 6 as it provided an opportunity to scrutinize its potential anti-infective properties. The results of these Se insertion reactions are portrayed in Scheme 2, as shown in FIG. 2.

As already mentioned above, transformation of 1 to 8,15-diisothiocyano-11(20)-amphilectene (2) via Se-catalyzed isothiocyanation was characterized by poor yields of the expected product (18%) and the recovery of starting material. In principle, a more efficient one-pot pathway could be based on diisoselenocyanation of 1 to 5 with Se (Scheme 2, Method A) followed by facile Se—S exchange in the presence of TEA to give 2 along lines demonstrated in Scheme 1. Indeed, the TEA-mediated Se—S exchange of 5 proceeds efficiently in THF upon refluxing for 4 h, and affords the expected diisothiocyanide 2 (71% yield). The results show that the Se—S exchange for 5 is considerably faster than the rate of C—Se bond insertion at the C-8 and C-15 isocyanides of 1.

With characterization data provided for all of the natural product hybrids, the synthesized compounds were evaluated in an in vitro growth inhibition assay against two *P. falciparum* Dd2 (drug resistant) and 3D7 (chloroquine-sensitive) malaria parasite lines, using the antimalarial drug chloroquine as reference standard. Concomitantly, compounds 1-6 were assayed against a laboratory strain of Mtb $H_{37}Rv$, using the antimycobacterial drug rifampicin as the control in the determination of the MIC value of each compound as shown in Table 1, wherein a=Tested as a 2:3 mixture of regioisomers; CQ=chloroquine and RMP=rifampicin (+Ctrls).

TABLE 1

In vitro antiplasmodial and antimycobacterial activity of compounds 1-6

| Compound | $IC_{50}$ Dd2 (µM) | $IC_{50}$ 3D7 (µM) | MABA MIC (µM) |
|---|---|---|---|
| 1 | 0.0031 | 0.0012 | 9.8 |
| 2 | 11.5863 | 11.7669 | 99.1 |
| 3 and 4$^a$ | 0.1433 | 0.3084 | 26.8 |
| 5 | 0.0066 | 0.0025 | 3.9 |
| 6 | 0.1490 | 0.1885 | 2.1 |
| CQ | 0.0519 | 0.0109 | — |
| RMP | — | — | 0.09 |

Active compounds were then assessed for potential cytotoxicity to human cells through the use of cultured Vero cells as shown in Table 2, wherein: a=Selectivity index (SI) defined by the ratio: $IC_{50}$ (in mammalian Vero cell lines)/$IC_{50}$ of antiparasitic activity against Dd2 (CQ-resistant strain) cell line; b=Selectivity index (SI) defined by the ratio: $IC_{50}$ (in mammalian Vero cell lines)/$IC_{50}$ of antiparasitic activity against 3D7 (CQ-sensitive strain) cell line; c=Selectivity index (SI) defined by the ratio: $IC_{50}$ (in mammalian Vero cell lines)/MIC of antimycobacterial activity against *M. tuberculosis* $H_{37}Rv$ cell line; d=Tested as a 2:3 mixture of regioisomers; and e=Value obtained from Ref. 24. CQ=chloroquine and RMP=rifampicin (+Ctrls). The values for cytotoxicity ($IC_{50}$) are calculated and compared to the $IC_{50}$ of antiparasitic activity and MIC of antimycobacterial activity values through calculation of a Selectivity Index (SI) for each compound through the following formulae: SI=$IC_{50}$/$IC_{50}$ of antiparasitic activity and SI=$IC_{50}$/MIC of antimycobacterial activity (shown in the far right columns of Table 2). A higher value indicates a higher degree of selectivity to *P. falciparum* and Mtb than to mammalian cells.

TABLE 2

Comparison of selectivity indexes of compounds 1-6 with CQ and RMP

| Compound | IC$_{50}$ Vero cell µM | SI$^a$ | SI$^b$ | SI$^c$ |
|---|---|---|---|---|
| 1 | 99.74 | 32174 | 83117 | 10.2 |
| 2 | >100 | >9 | >8 | >1.0 |
| 3 and 4$^d$ | 78.14 | 545 | 253 | 2.9 |
| 5 | 48.55 | 7356 | 19420 | 12.4 |
| 6 | 95.22 | 639 | 505 | 45.3 |
| CQ | 234.47$^e$ | 4518 | 21511 | — |
| RMP | >100 | — | — | >1100 |

Except for the diisothiocyanate-functionalized amphilectane diterpene 2, all of the isoselenocyanate hybrids (3-6) showed sub-micro molar in vitro antiplasmodial activity (0.0025-0.3084 µM) against the two malaria parasite lines screened. Among these hybrids, only compound 5 having two isoselenocyanate functionalities showed more activity with Dd2 IC$_{50}$=0.0066 and 3D7 IC$_{50}$=0.0025 µM when compared to the standard drug chloroquine (Dd2 IC$_{50}$=0.0519 µM, 3D7 IC$_{50}$=0.0109 µM). Remarkably, hybrid 5 showed less toxicity (SI=7356) than chloroquine (SI=4518) against the drug resistant *P. falciparum* Dd2 strain. In the end, however, starting scaffold 1 with two isocyanide groups proved to be the most promising compound of the series (Dd2 IC$_{50}$=0.0031 µM, 3D7 IC$_{50}$=0.0012 µM), which was manifold times more active and less toxic than the standard drug (Tables 1 and 2). Interestingly, previous work by Konig et. al. has demonstrated that as for inhibition against *P. falciparum* the exchange of the isocyanide against the isocyanate group always results in a more significant drop in potency when compared to the —NC⇒—NCS exchange. On the other hand, our data suggest that switching the isocyanide for the isoselenocyanate functionality leads to no significant loss in antiparasitic activity. Altogether, the most notable results obtained from this limited series of compounds are those for 3-6. To our knowledge, this is the first report of isoselenocyanate-functionalized inhibitors of *P. falciparum*.

| Mass | Calc. Mass | mDa | PPM | DBE | i-FIT | Formula |
|---|---|---|---|---|---|---|
| 388.2007 | 388.2007 | 0.0 | 0.0 | 8.0 | 134.0 | C$_{22}$H$_{32}$N$_2$S$_2$$^a$ |
| 436.1459 | 436.1451 | 0.8 | 1.8 | 9.0 | 9.4 | C$_{22}$H$_{32}$N$_2$S$^{80}$Se$^b$ |
| 484.0902 | 484.0896 | 0.6 | 1.2 | 10.0 | 1116.0 | C$_{22}$H$_{32}$N$_2$$^{80}$Se$_2$$^c$ |
| 377.1626 | 377.1622 | 0.4 | 1.1 | 8.0 | 58.8 | C$_{21}$H$_{31}$N$^{80}$Se$^d$ |

When screened for in vitro activity against Mtb H$_{37}$Rv in a microbroth dilution assay, the best (lowest) MIC values of 3.9 and 2.1 µM, respectively, were determined for isoselenocyanate-functionalized hybrids 5 and 6. On the other hand, hybrids with an isothiocyanate moiety (2-4) had the worst (highest) MIC's (26.8-99.1 µM) as shown in Table 1. Interestingly, amphilectane-based diterpene 6 with a single isoselenocyanate moiety was identified as both the most potent (MIC=2.1 µM) and the least toxic (the highest SI value of 45.3 was determined for 6) of the series (Table 2). Given its good MIC and SI, analog 6 is a potential candidate for efficacy studies in mice, and should future collaborations demonstrate that this isoselenocyanate-functionalized amphilectane diterpene has good pharmacokinetic properties, it could become a new anti-TB drug.

Despite the high toxicity of many selenium compounds, organic derivatives of selenium have been previously synthesized for medical applications. As a result, selenium-containing compounds are of increasing interest because of their chemical properties and biological activities. While based on a very limited library of hybrid compounds, this invention demonstrates for the first time that isoselenocyanate-functionalized amphilectane diterpenes could become important antimalarial and anti-TB pharmacophores.

Although the present invention has been described herein with reference to the foregoing exemplary embodiment, this embodiment does not serve to limit the scope of the present invention. Accordingly, those skilled in the art to which the present invention pertains will appreciate that various modifications are possible, without departing from the technical spirit of the present invention.

We claim:

1. An anti-infective functionalized amphilectane diterpene selected from the group consisting of the following compounds:

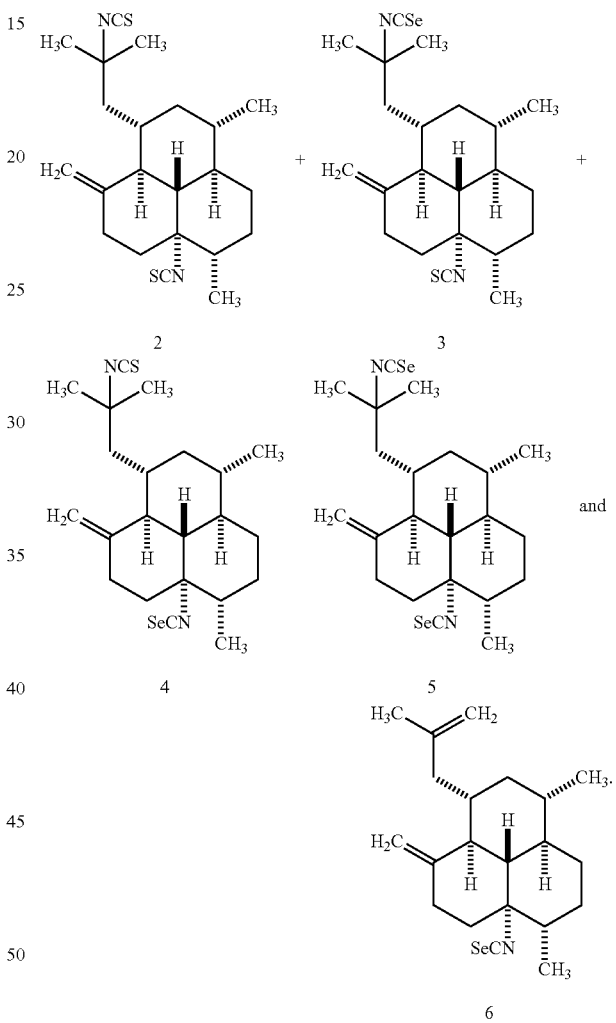

2. The anti-infective functionalized amphilectane diterpene of claim 1, wherein said functionalized amphilectane diterpene is 8,15-Diisothiocyano-11(20)-amphilectene.

3. The anti-infective functionalized amphilectane diterpene of claim 1, wherein said functionalized amphilectane diterpene is 8-Isothiocyano-15-isoselenocyano-11(20)-amphilectene.

4. The anti-infective functionalized amphilectane diterpene of claim 1, wherein said functionalized amphilectane diterpene is 8-Isoselenocyano-15-isothiocyano-11(20)-amphilectene.

5. The anti-infective functionalized amphilectane diterpene of claim 1, wherein said functionalized amphilectane diterpene is 8,15-Diisoselenocyano-11(20)-amphilectene.

6. The anti-infective functionalized amphilectane diterpene of claim 1, wherein said functionalized amphilectane diterpene is 8-Isoselenocyanoamphilecta-11(20),15-diene.

7. A method of synthesizing an anti-infective functionalized amphilectane diterpene selected from the group consisting of the following compounds:

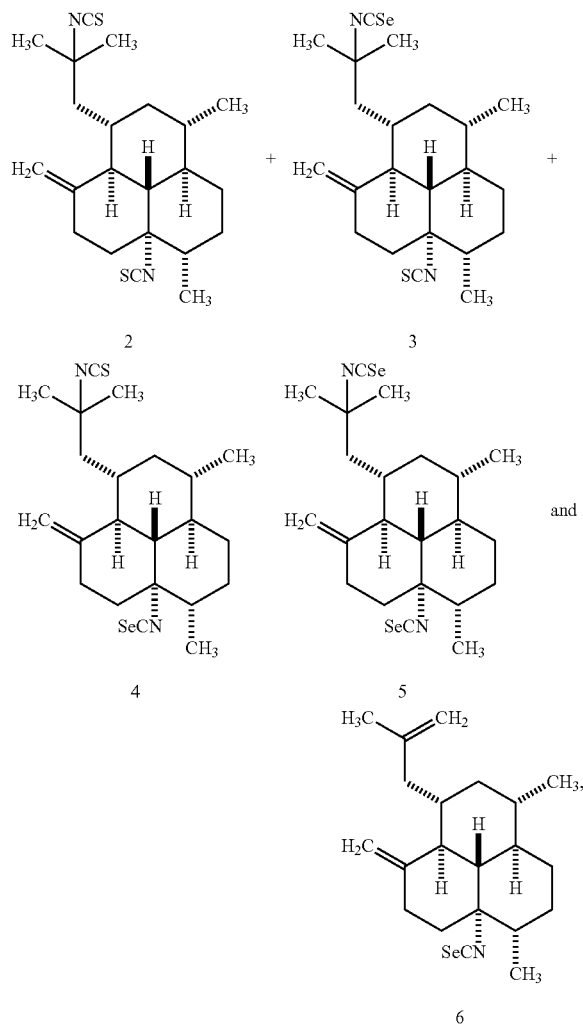

the method comprising isothio- or isoselenocyanating a metabolite with the chemical formula:

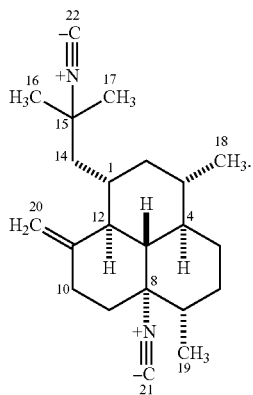

8. The method of claim 7, wherein said anti-infective functionalized amphilectane diterpene is synthesized by the isothiocyanation of (−)-8,15-diisocyano-11(20)-amphilectene.

9. The method of claim 7, wherein said anti-infective functionalized amphilectane diterpene is synthesized by the isoselenocyanation of (−)-8,15-diisocyano-11(20)-amphilectene.

10. The method of claim 8, wherein said anti-infective functionalized amphilectane diterpene is 8,15-Diisothiocyano-11(20)-amphilectene.

11. The method of claim 8, wherein said anti-infective functionalized amphilectane diterpene is 8-Isothiocyano-15-isoselenocyano-11(20)-amphilectene.

12. The method of claim 8, wherein said anti-infective functionalized amphilectane diterpene is 8-Isoselenocyano-15-isothiocyano-11(20)-amphilectene.

13. The method of claim 9, wherein said anti-infective functionalized amphilectane diterpene is 8,15-Diisoselenocyano-11(20)-amphilectene.

14. The method of claim 9, wherein said anti-infective functionalized amphilectane diterpene is 8,15-Diisothiocyano-11(20)-amphilectene.

* * * * *